United States Patent [19]
Bolduc et al.

[11] Patent Number: 5,951,575
[45] Date of Patent: Sep. 14, 1999

[54] APPARATUS AND METHODS FOR ROTATIONALLY DEPLOYING NEEDLES

[75] Inventors: Lee R. Bolduc, Mountain View; Alan R. Rapacki, San Francisco, both of Calif.

[73] Assignee: Heartport, Inc., Redwood City, Calif.

[21] Appl. No.: 08/609,809

[22] Filed: Mar. 1, 1996

[51] Int. Cl.$^6$ .................................................. A61B 17/04
[52] U.S. Cl. ........................ 606/144; 606/139; 606/148
[58] Field of Search ........................... 606/144, 145, 606/139, 148, 205, 206, 208

[56] References Cited

U.S. PATENT DOCUMENTS

| | | | |
|---|---|---|---|
| 3,638,654 | 2/1972 | Akuba | 128/340 |
| 4,165,745 | 8/1979 | Heifetz | 128/318 |
| 4,491,135 | 1/1985 | Klein | 128/340 |
| 4,557,265 | 12/1985 | Andersson | 128/340 |
| 4,580,567 | 4/1986 | Schweitzer et al. | 128/340 |
| 4,597,390 | 7/1986 | Mulhollan et al. | 128/340 |
| 4,621,640 | 11/1986 | Mulhollan et al. | 128/340 |
| 4,747,358 | 5/1988 | Moll et al. | 112/169 |
| 4,938,214 | 7/1990 | Specht et al. | 128/340 |
| 4,953,558 | 9/1990 | Akerfeldt | 128/751 |
| 5,015,250 | 5/1991 | Foster | 606/147 |
| 5,037,433 | 8/1991 | Wilk et al. | 606/139 |
| 5,147,373 | 9/1992 | Ferzli | 606/144 |
| 5,201,743 | 4/1993 | Haber et al. | 606/147 |
| 5,209,747 | 5/1993 | Knoepfler | 606/16 |
| 5,224,948 | 7/1993 | Abe et al. | 606/147 |
| 5,254,130 | 10/1993 | Poncet et al. | 606/206 |
| 5,281,235 | 1/1994 | Haber et al. | 606/139 |
| 5,306,281 | 4/1994 | Beurrier | 606/144 |
| 5,308,353 | 5/1994 | Beurrier | 606/144 |
| 5,374,277 | 12/1994 | Hassler | 606/207 |
| 5,376,096 | 12/1994 | Foster | 606/147 |
| 5,383,886 | 1/1995 | Kensey et al. | 606/185 |
| 5,389,103 | 2/1995 | Melzer et al. | 606/144 |
| 5,391,174 | 2/1995 | Weston | 606/148 |
| 5,411,613 | 5/1995 | Rizk et al. | 606/148 |
| 5,417,203 | 5/1995 | Tovey et al. | 128/4 |
| 5,474,571 | 12/1995 | Lang | 606/205 |
| 5,486,185 | 1/1996 | Freitas et al. | 606/142 |
| 5,643,294 | 7/1997 | Tovey . | |
| 5,649,955 | 7/1997 | Hashimoto et al. | 606/205 |

FOREIGN PATENT DOCUMENTS

| | | |
|---|---|---|
| 0 934 141 A1 | 1/1995 | European Pat. Off. . |
| WO 94/28801 | 12/1994 | WIPO . |

OTHER PUBLICATIONS

Melzer, A. et al., "Future Trends in Endoscopic Suturing", 1994, *End. Surg.*, vol. 2, pp. 78–82.

*Primary Examiner*—Michael Buiz
*Assistant Examiner*—Tina T. D. Pham
*Attorney, Agent, or Firm*—Jens E. Hoekendijk; Jeffry J. Grainger

[57] ABSTRACT

A surgical instrument comprises a shaft, a clamp support at a distal end of the shaft, and a clamp comprising a pair of pivotally mounted jaws within the clamp support. A handle at a proximal end of the shaft comprises an actuator for both opening and closing the jaws of the clamp and for rotating the jaws of the clamp about a deflected axis defined by the clamp support. The actuator includes a lever and a rotatable wheel which are coupled to the clamp via a flexible drive cable extending through the shaft and clamp support. The device is particularly useful for manipulating and driving curved surgical needles in thoracoscopic, laparoscopic, and other endoscopic suturing procedures.

23 Claims, 8 Drawing Sheets

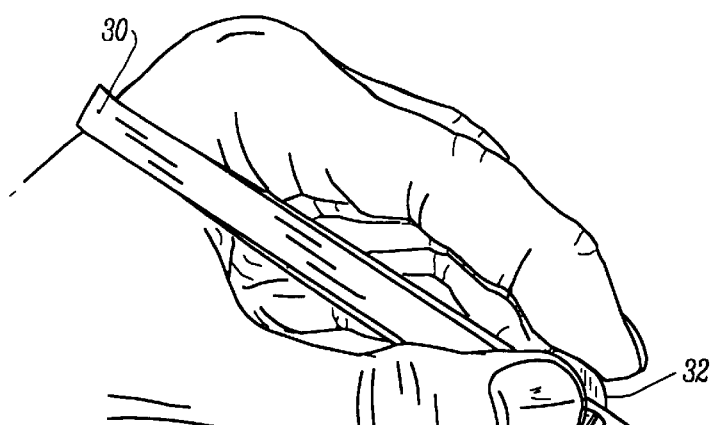
FIG. 6
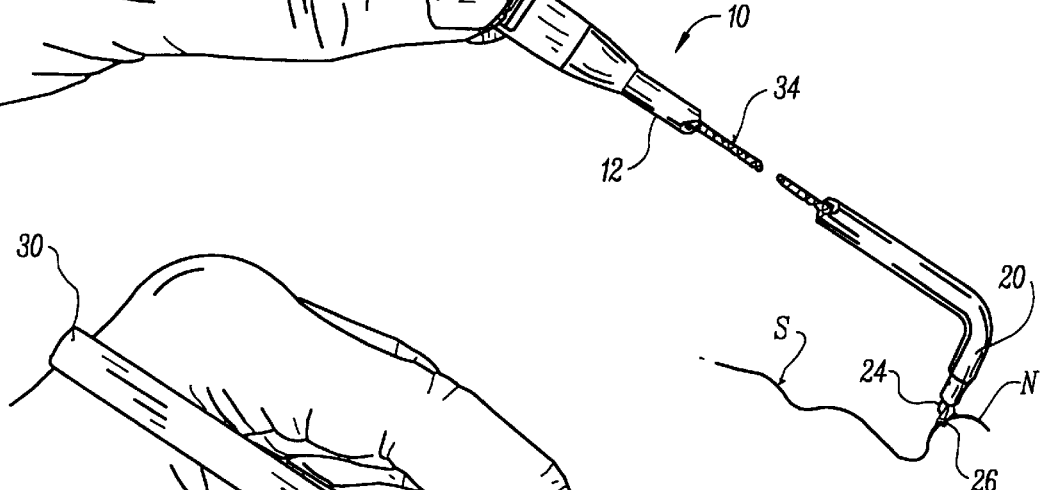
FIG. 7
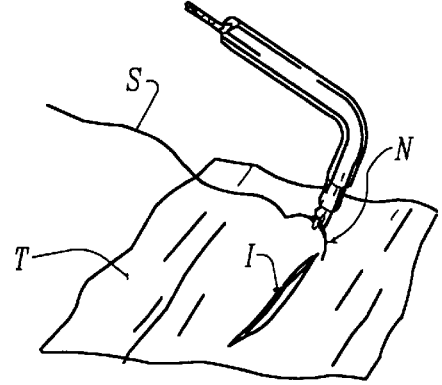

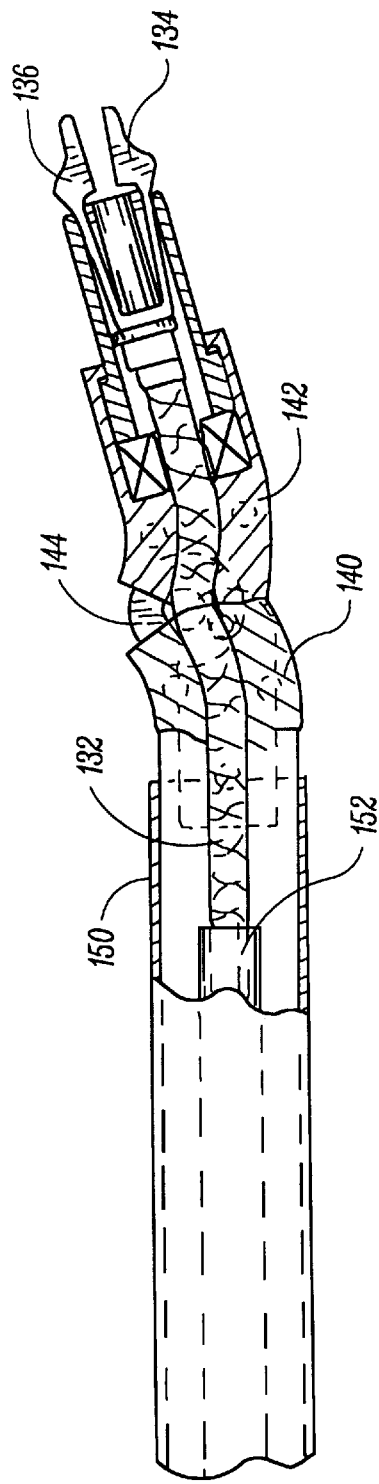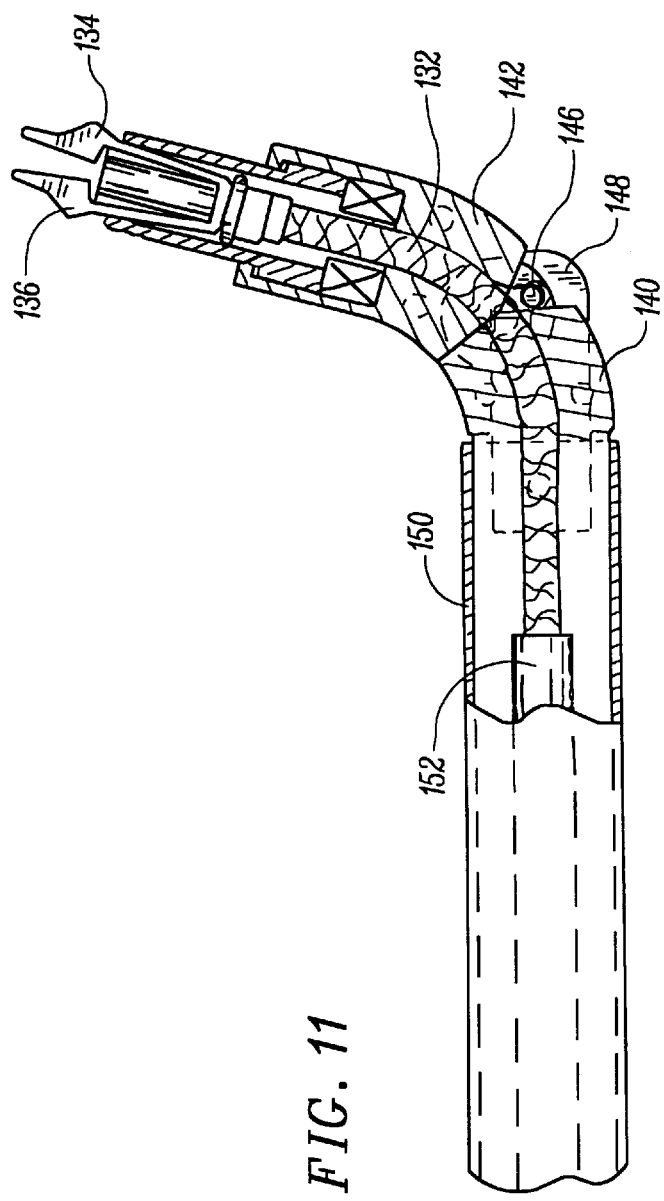

APPARATUS AND METHODS FOR ROTATIONALLY DEPLOYING NEEDLES

BACKGROUND OF THE INVENTION

1. Field of the Invention

The present invention relates generally to apparatus and methods for the remote manipulation of surgical needles and other articles. More particularly, the present invention relates to the construction and use of a needle driver which can rotate a curved needle about an axis which is non-coaxial with the axis of the needle driver.

Thoracoscopic, laparoscopic, and other endoscopic surgical procedures are complicated by the need to pass surgical instruments through trocars and other access ports having very small diameters, typically 1 cm or below in diameter. Endoscopic suturing is a particularly time-consuming and tedious process since the ability to "roll" a curved needle through an arc is quite limited. While a variety of endoscopic needle drivers are available, most such needle drivers provide for rotation of the needle through an arc about an axis which is aligned with the axis of the driver itself. Such a configuration makes suturing very difficult in a variety of circumstances.

It would thus be desirable to provide improved apparatus and methods for manipulating surgical needles and other articles in a variety of surgical procedures. It would be particularly desirable to provide improved apparatus and methods for driving curved surgical needles for suturing in thoracoscopic, laparoscopic, and other endoscopic surgical procedures. Such apparatus and methods will preferably provide for rotation of curved surgical needles through an arc about an axis which is oriented at an angle relative to the shaft of the apparatus. Even more preferably, it would be desirable if the apparatus and method provided for holding the needle in a radially offset position relative to the shaft while the needle is being rotated about the angle. The method and instrument should further provide for selective and firm grasping of the needle and for easy and convenient rotation of the needle after it has been grasped. The overall design of the apparatus should facilitate viewing of the needle during both open and endoscopic procedures. It would be still further desirable if the instrument and methods of the present invention were useful for procedures in addition to needle driving and suturing.

2. Description of the Background Art

Needle drivers having jaws disposed on angled or articulated distal ends are disclosed in U.S. Pat. Nos. 5,417,203 and 5,209,747, and Melzer et al. (1994) *End. Surg.* 2:78–82. Jaw actuation mechanisms for suturing and other laparoscopic procedures are described in U.S. Pat. Nos. 5,281,235; 5,201,743; 5,147,373; 4,580,567; 4,491,135; and 4,165,745. In some cases, the jaw is rotatable about its axis for turning a needle or other purposes. See, for example, U.S. Pat. Nos. 5,147,373 and 4,491,135. Needle drivers having arcuate drive mechanisms are described in U.S. Pat. Nos. 5,391,174; 5,376,096; 5,308,353; 5,224,948; 5,015,250; 4,938,214; 4,621,640; 4,597,390; 4,557,265; and 3,638,654; EP 634 141; and WO 94/28801. Other suturing and needle manipulation devices are described in U.S. Pat. Nos. 5,389,103; 5,306,281; 5,037,433; 4,953,558; and 4,747,358.

SUMMARY OF THE INVENTION

The present invention provides improved apparatus and methods for thoracoscopic, laparoscopic, and other endoscopic suturing and related surgical procedures. The apparatus provide for rotational driving of curved surgical needles through an arc which is disposed at an angle relative to a longitudinal axis of the apparatus, usually at an angle from 45° to 135°, typically although not necessarily being about 90°. By providing for rotation which is not aligned with the axis of the apparatus, the user can "roll" the needle through tissue surfaces which are oriented in planes which are generally normal to the longitudinal axis of the apparatus. Moreover, by radially offsetting the needle from the axis of the device, visibility of the needle and target site within the tissue is greatly improved. The structure of the device of the present invention will also permit single-handed operation, where a needle can be grasped, rotated, and subsequently released from the device using one hand while the other hand remains free for other purposes. Although specifically intended as a needle driver, the devices of the present invention could also be used as scissors, biopsy devices, nibblers, or other devices which employ opposed jaws.

In a first aspect of the present invention, a suturing instrument comprises a shaft having a proximal end, a distal end, and a longitudinal axis. A support is attached to the distal end of the shaft and defines a deflected or non-aligned axis relative to the shaft. Usually, the support will be attached to or integral with the shaft (e.g. as an extension of the shaft) so that the angle is fixed relative to the longitudinal axis of the shaft. In other cases, however, the support can be joined to the shaft with an articulated, flexible, hinged, or other joint which permits positioning of the support relative to the shaft so that the angle of the deflected axis relative to the longitudinal axis of the shaft can be adjusted. In all cases, a pair of jaws or a clamp will be mounted on the support, where the clamp is suitable for grasping surgical needles, and other surgical articles which are desired to be manipulated. A clamp actuator is disposed at the proximal end of the shaft and can be actuated to shift the clamp between an open configuration and a closed configuration for grasping the needle or other article. A clamp rotator is also disposed at the proximal end of the shaft and is actuable to rotate the clamp about the axis defined by the support. In this way, needles and other articles can be selectively grasped, rotated about the non-aligned axis, released, and regrasped by manipulating the proximal end of the shaft.

The surgical instrument will usually be of a type suitable for thoracoscopic, laparoscopic, and other endoscopic procedures, where the shaft typically has a length in the range from 5 cm to 15 cm and a maximum cross-sectional width in the range from 5 mm to 10 mm. The instrument will usually further comprise a handle, where the clamp actuator and clamp rotator are disposed on or within the handle. In a preferred embodiment, the shaft and support, e.g. in the form of a shaft extension, each have central lumens and a flexible drive cable is disposed from the proximal end of the shaft to the distal end of the shaft extension. The clamps will usually comprise a pair of pivotally attached jaw elements attached to the distal end of the drive cable, where the jaws may be opened and closed by axially reciprocating the drive cable and rotated by rotating the drive cable. Usually, a fixed surface will be provided at or near the distal end of the shaft extension so that axial reciprocation of the jaws engages a cam surface on each jaw against the fixed surface, resulting in opening and closing of the jaws.

In a second aspect of the present invention, a needle driver comprises a shaft having a proximal end, a distal end, and a lumen therebetween. The lumen is bent or curved from a longitudinal direction at its proximal end to an angled direction at its distal end, more usually being in a J-shaped or L-shaped configuration where the lumen is straight along most of the length of the shaft, and deflected at a preselected or variable angle at its distal end. A pair of pivotally attached jaws are mounted in the distal end of the shaft lumen, and a drive cable extending through the lumen is connected at its distal end to the jaws. An actuator is disposed at the proximal end of the shaft and is coupled to the drive cable to shift the jaws between an extended, open configuration and a retracted, closed configuration. Additionally, the actuator can rotate the cable to rotate the jaws about the angled axis defined by the distal end of the lumen.

Usually, the needle driver will be configured for thoracoscopic, laparoscopic, and other endoscopic procedures, typically having the shaft dimensions set forth above. As a result of the deflected distal portion of the shaft and shaft lumen, the jaws will be radially offset from the axis of the proximal section of the shaft, preferably by a distance in the range from 5 mm to 20 mm. Usually, the distal end of the lumen will lie at an angle in the range from about 45° to about 135°, preferably about 70° to about 110°, relative to the axis of the proximal section of the shaft.

In the exemplary embodiment of the needle driver, the jaws are normally open, typically joined by a resilient hinge, and are closed by drawing the drive cable in a proximal direction to engage the individual jaw elements against the fixed surface to close the jaws. The actuator comprises a handle, a shuttle secured to the proximal end of the drive cable and slidably mounted within the handle, and a retractor secured between the handle and the shuttle to selectively retract the shuttle to close the jaws by drawing proximally on the drive cable. More usually, the actuator further comprises a rotator secured between the shuttle and the proximal end of the drive cable to selectively rotate the jaws about the axis. Typically, the retractor comprises a lever and a link connected as a three-bar linkage to retract the shuttle. The rotator comprises a wheel rotatably mounted on the shuttle and a gear attached to the proximal end of the drive cable, where the wheel engages the gear so that manual rotation of the wheel rotates the drive cable and thus the jaws.

Alternatively, the actuator may comprise a powered motor, typically an electric motor, mounted on the shuttle in place of the rotator described above. The electric motor will typically be battery driven, with the battery also being mounted on the shuttle. The retractor mechanism may be the same as described above. A switch or other actuator is provided for the motor, typically being located on the handle. The jaws can thus be opened and closed using the lever, as described above, while rotation of the jaws is effected using the motor.

According to the method of the present invention, curved surgical needles are rotated through an arc by first manipulating a proximal end of a shaft to position a distal end of the shaft at a target site within a patient body. A surgical needle which is curved in an arc is then grasped and the arc of the needle is rotated about an axis which is at an angle to a longitudinal axis of the shaft. Usually, the angle is in the range from 45° to 135°, more usually from about 70° to about 110° relative to the longitudinal axis. The manipulating step typically comprises passing a distal end of the shaft into a body cavity through a percutaneous access port, such as a trocar or other tissue-retracting element commonly used in thoracoscopic, laparoscopic, or other endoscopic procedures. The grasping step typically comprises clamping a pair of jaws onto the needle, usually by retracting a pair of normally open jaws against a cam surface to close the jaws. The retracting step will usually comprise tensioning a drive cable which extends through the shaft and which is attached at its distal end to the jaws. The rotating step typically comprises rotating the jaws about the axis, usually by rotating the drive cable. Rotation of the drive cable may be achieved either manually using a drive wheel which is connected to the shaft through a suitable mechanical linkage or by an electric or other motor which is attached to the drive cable. The methods may also include the steps of releasing the needle from the shaft after the step of rotating and regrasping the needle to draw the needle through the tissue, which steps are performed without removing the distal end of the shaft from the body cavity. The methods of the present invention provide for improved control of the needles while they are being manipulated, most notably by permitting curved surgical needles to be rolled through tissue which is oriented in a plane generally normal to the axis of the needle driver. By positioning the needle radially outward from the shaft of the instrument, visibility of the suturing process is also improved.

BRIEF DESCRIPTION OF THE DRAWINGS

FIGS. 6–8 illustrate use of the device of FIG. 1 for grasping and driving a surgical needle in accordance with the method of the present invention.

FIG. 10 is a detailed view of the deflectable tip of the instrument of FIGS. 9 and 9A, shown in partial section with the tip in its relatively straight configuration.

FIG. 11 is a view similar to FIG. 10, shown with the tip in its fully deflected configuration.

DESCRIPTION OF THE SPECIFIC EMBODIMENTS

Figure 1:
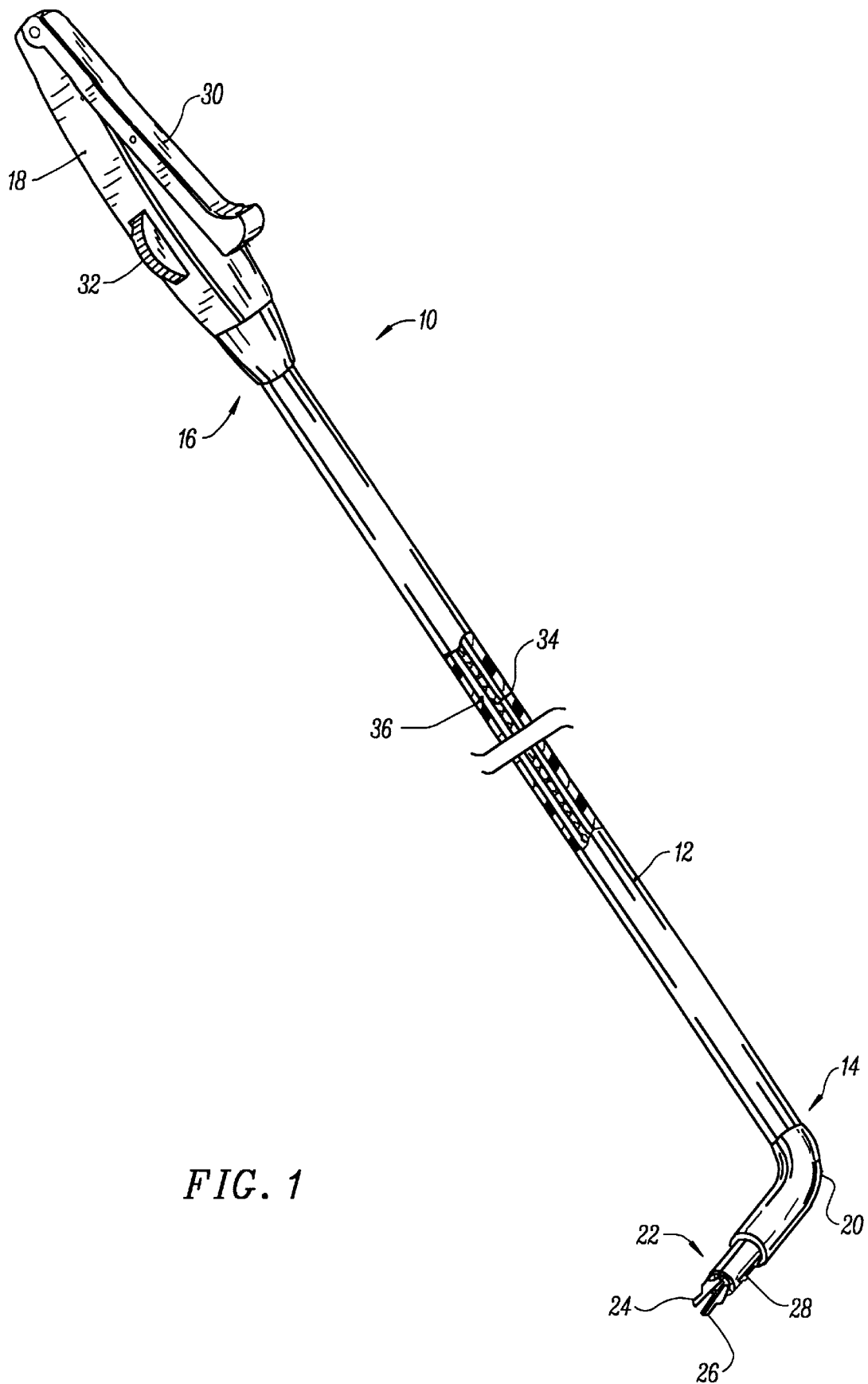
FIG. 1 is a perspective view of a surgical instrument constructed in accordance with the principles of the present invention.

Apparatus according to the present invention include needle drivers and other surgical instruments comprising a shaft, a clamp at a distal end of the shaft, and a clamp actuator and rotator at a proximal end of the shaft. The shaft will be of a type generally suitable for thoracoscopic, laparoscopic, and other endoscopic surgical procedures, and will thus typically have a maximum cross-sectional dimension which permits passage through normal percutaneous access devices, such as trocars. The maximum dimension will usually be less than 15 mm, more usually being in the range from 5 mm to 12 mm, and preferably being in the range from 5 mm to 10 mm. The length of the shaft will vary depending on its intended use, typically being in the range from 5 cm to 20 cm, more typically in the range from 10 cm to 15 cm. Many thoracoscopic procedures will require relatively short shafts, typically having a length from 5 cm to 10 cm, while many laparoscopic procedures will generally require a longer shaft length, typically in the range from 10 cm to 20 cm. The shaft may be fabricated from conventional materials, such as metals, e.g., surgical stainless steels, plastics, and the like. Reusable devices will generally be sterilizable and made of metal, while disposable devices will often be made of plastics.

The apparatus of the present invention will have a support structure or assembly disposed at the distal end of the shaft for holding a clamp component in a desired orientation and configuration. In particular, the support will define a deflected or deflectable axis and will usually also provide for radial offset of the clamp from the axis of the shaft. The support may be formed as a separate component from the shaft, or may be formed as an integral extension of the shaft. In either case, the support will usually provide for a curved, angled, or otherwise deflected extension from the shaft so that the distal end of the support is oriented at the desired angle, and at a desired radial offset distance from the longitudinal axis of the shaft. Suitable angles are in the range from about 45° to about 135°, preferably from about 60° to about 120°, and typically about 60° to about 90° relative to the longitudinal axis. The radial offset of the support (which is the distance at which the clamp is maintained from the shaft) will typically be in the range from 5 mm to 20 mm, preferably from 10 mm to 15 mm.

In the exemplary embodiments, the support is shown as a fixed structure having an invariant geometry. In certain circumstances, it may be desirable to provide support structures which can be adjusted to change the angle and/or radial offset distance relative to the longitudinal axis of the proximal portion of the shaft. Such adjustable support structures can employ a variety of conventional mechanical designs, such as hinges, universal joints, flexible sleeve structures, and the like. Such structures may be adjustable remotely, i.e., from the proximal end of the device, or may be adjustable only by direct shaping or manipulation of the distal end of the device.

A clamp structure will be disposed at the distal end of the support. The clamp may be any structure, component, or device, that can be selectively actuated to grasp a needle or other article by manipulation from the proximal end of the apparatus. The clamp will usually comprise a pair of actuable jaws, more usually comprising pivotally connected jaws, but also including parallel (caliper-type) jaws. The clamp has opposing surfaces movable toward and away from each other to permit selective clamping of a needle or other article. The jaws will preferably be configured to grasp a curved needle so that the needle may be rolled or rotated about an axis parallel to the needle's axis of curvature, and the opposed surfaces of the jaws may be textured, e.g., with teeth, for improved gripping ability, or could be flat. A variety of other clamping mechanisms will also be suitable. In addition to clamping mechanisms, the proposed jaws of the present invention can be used as scissors, biopsy devices, nibblers, rongeurs, other cutting devices, and the like.

The clamp will be mounted on the support so that it can be both (1) open and closed, and (2) rotated about the axis defined by the support. A variety of mechanical assemblies can be used to provide for such actuation and rotation, including gears, rods, micromotors, shape memory alloy actuators, and the like. In the exemplary embodiment, a flexible drive cable is disposed within a continuous central lumen passing through the shaft and the support structure. The drive cable is connected to the pivotally attached jaws.

The jaws may thus be open and closed by axially translating the drive cable to selectively engage cam surfaces on the jaws against a fixed surface on or near the support to open or close the jaws in response to the axial motion. The jaws may be directly rotated by rotating the drive cable from the proximal end thereof.

One or more actuators will be provided at the proximal end of the shaft, typically in or on a handle structure which is attached at the proximal end of the shaft. The actuator(s) will provide for both reciprocation and rotation of the flexible drive cable in order to actuate the jaws as desired. An exemplary design employs a shuttle which is attached to the proximal end of the flexible drive cab and which is slidably mounted within the handle. Axial translation of the shuttle within the handle thus opens and closes the jaws at the distal end of the shaft. A mechanism for rotating the drive cable is mounted directly on the shuttle, typically including a wheel and gear to provide for a mechanical advantage when rotating the cable. Advantageously, the rotational actuator is operable independently of the jaw or clamping actuator so that the jaws may be selectively opened and closed at any rotational position. A variety of other such actuators can also be provided for coupling to the drive cable to reciprocate and rotate the jaws. For example, rotational actuation can be achieved using a motor, typically an electric motor, which can be mounted to reciprocate on the shuttle. Rotation can thus be achieved using a simple three-way switch mounted on the handle, so that the jaws can be selectively rotated in the clockwise or counter-clockwise direction.

Referring now to FIG. 1, an exemplary needle driver 10 constructed in accordance with the principles of the present invention will be described. It will be appreciated that, although particularly intended for manipulating and driving surgical needles as part of thoracoscopic, laparoscopic, and endoscopic suturing procedures, the apparatus 10 could also find other uses in surgical procedures where it is desired to manipulate articles in addition to needles about angled axes and at distances spaced radially outward from the device shaft. Other articles include probes, catheters, electrodes, prosthetic devices, and the like.

The driver 10 comprises a shaft 12 having a distal end 14 and a proximal end 16, a handle 18 secured to the proximal end 16, and a needle support 20 attached to the distal end 14. A clamp device 22 comprises a pair of jaw elements 24 and 26 which are mounted in a collar 28 which extends from the distal-most tip of the needle support 20. The handle 18 comprises a lever 30 and a rotation wheel 32 which are used for actuating (opening and closing) and rotating the clamp device 22, respectively, as will be described in detail below. A flexible drive cable 34 extends through a central lumen 36 of the shaft 12 and is connected at its proximal end to the lever 30 and wheel 32 (as described below) and at its distal end to the clamp device 22 (also as described below).

Figure 2:
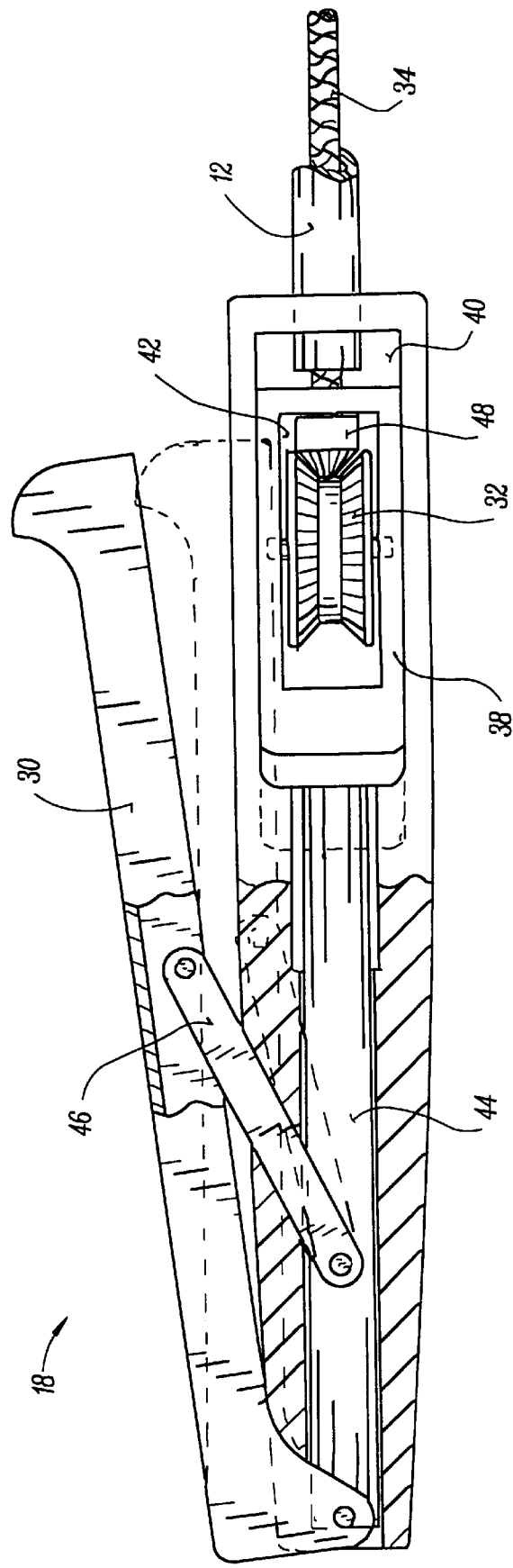
FIG. 2 is a detailed view of the handle of the instrument of FIG. 1, shown in section with an actuated configuration shown in broken line.

Referring now to FIG. 2, construction and operation of the handle 18 will be described in more detail. A shuttle 38 is mounted within a slot 40 of the handle 18 near its distal end. The shuttle 38 carries the rotatable wheel 32 in an opening 42 therein. The shuttle 38 is connected at its proximal end to a rod 44 which is also slidably mounted in the handle 18. The rod 44, in turn, is connected to lever 30 by a link 46 which is pivotally attached to the rod and lever, respectively, to form a three-bar linkage assembly. In this way, depression of the lever 30 (i.e., depression of the lever toward the main body of the handle 18) causes rod 44 to move in the proximal direction, as illustrated in broken line in FIG. 2. Such motion causes the shuttle 38 to also move proximally, applying tension to the proximal end of drive cable 34. The drive cable 34 will be selected to have sufficient tensile strength so that tension applied at its proximal end will axially retract the clamp device 22, as described in more detail below. The drive cable 34 will also have sufficient rotational rigidity so that rotation of the drive cable will rotate the clamp assembly, also as described below. Suitable drive cables may be braided, counterwound helices, or other suitable cable structures having the requisite tensile strength and torsional rigidity.

Rotation of the drive cable 34 is effected using the rotatable wheel 32 within the shuttle 38. The rotatable wheel 32 engages a rotatable gear 48 which is attached directly to the proximal end of the drive cable 34 within the opening 42 in the shuttle 38. The design and construction of such wheel and gear assemblies are well known and need not be described further. It will be appreciated that handle 18 thus provides for opening and closing of the jaw elements 24 and 26 of clamp device 22 by depressing and releasing the lever 30, while the clamp device 22 may be simultaneously rotated by rotation of the rotatable wheel 32. Such motions can conveniently be achieved using a single hand, as will be illustrated and described in more detail below. As described in more detail below, it is also possible to employ an electric motor mounted on the shuttle for rotating the drive cable.

Figure 3:
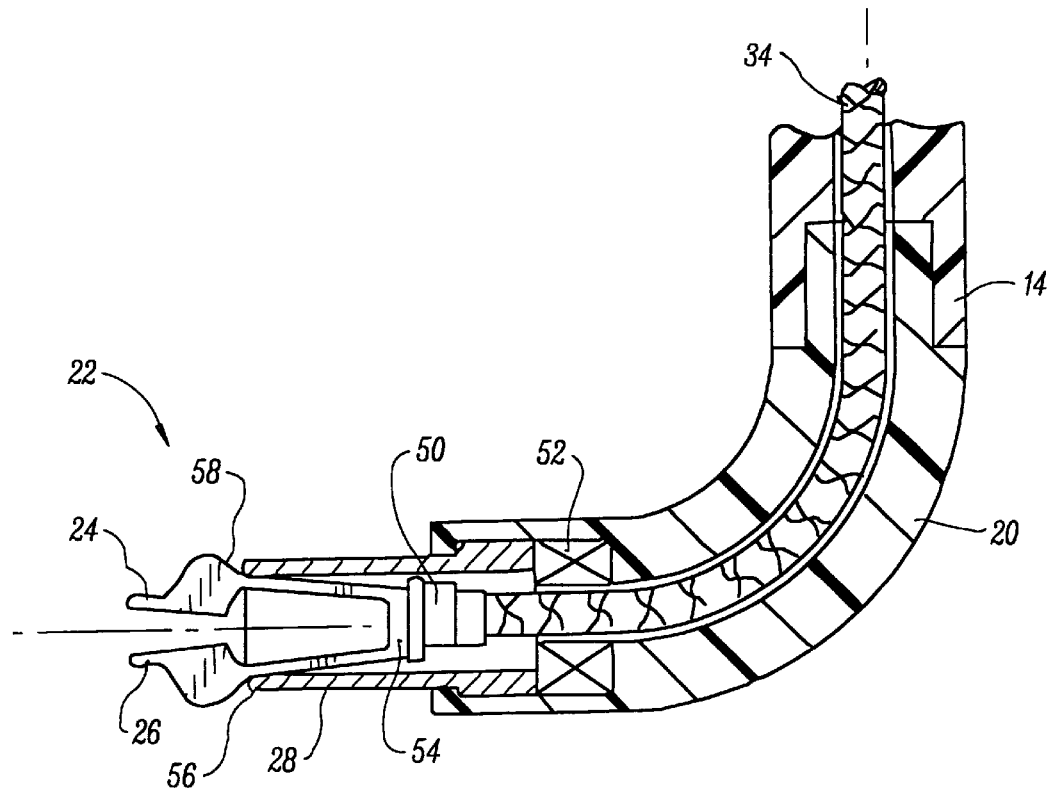
FIG. 3 is a detailed view of the distal end of the instrument of FIG. 1, shown with the needle-grasping jaws in their open configuration.
Figure 4:
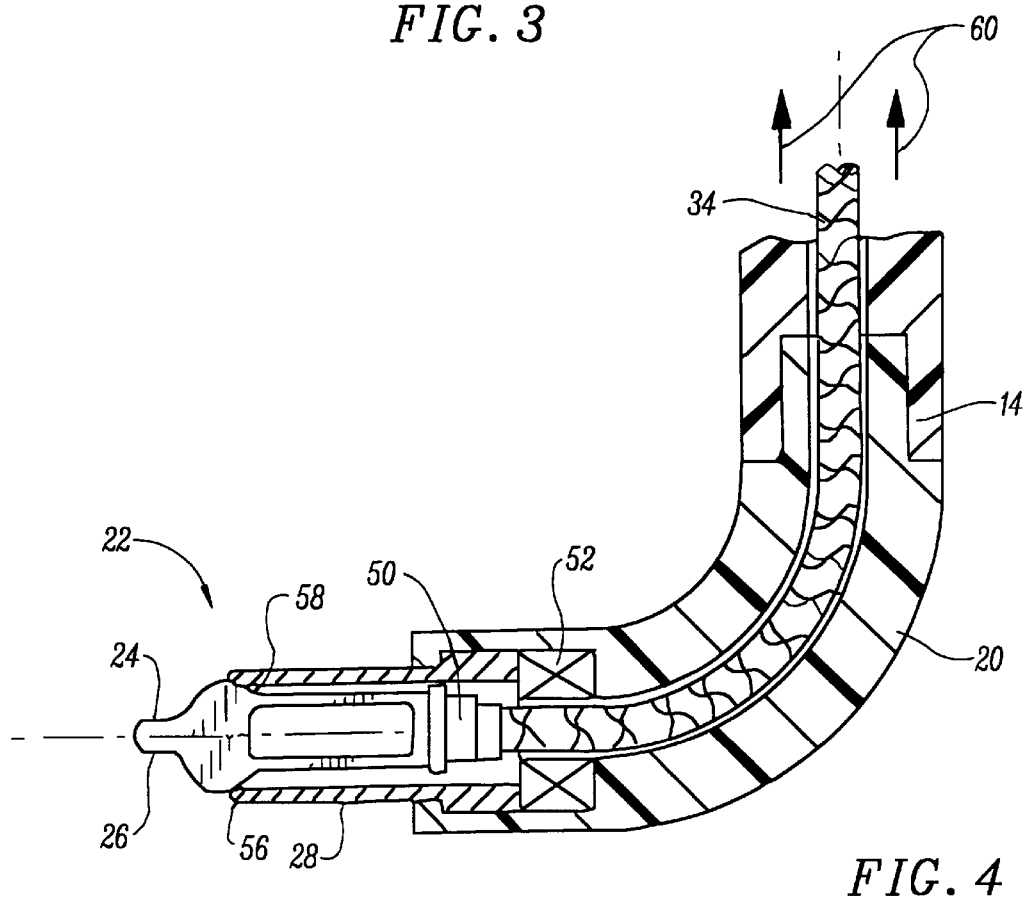
FIG. 4 is a view similar to FIG. 3, shown with the needle-grasping jaws in their closed configuration.
Figure 5:
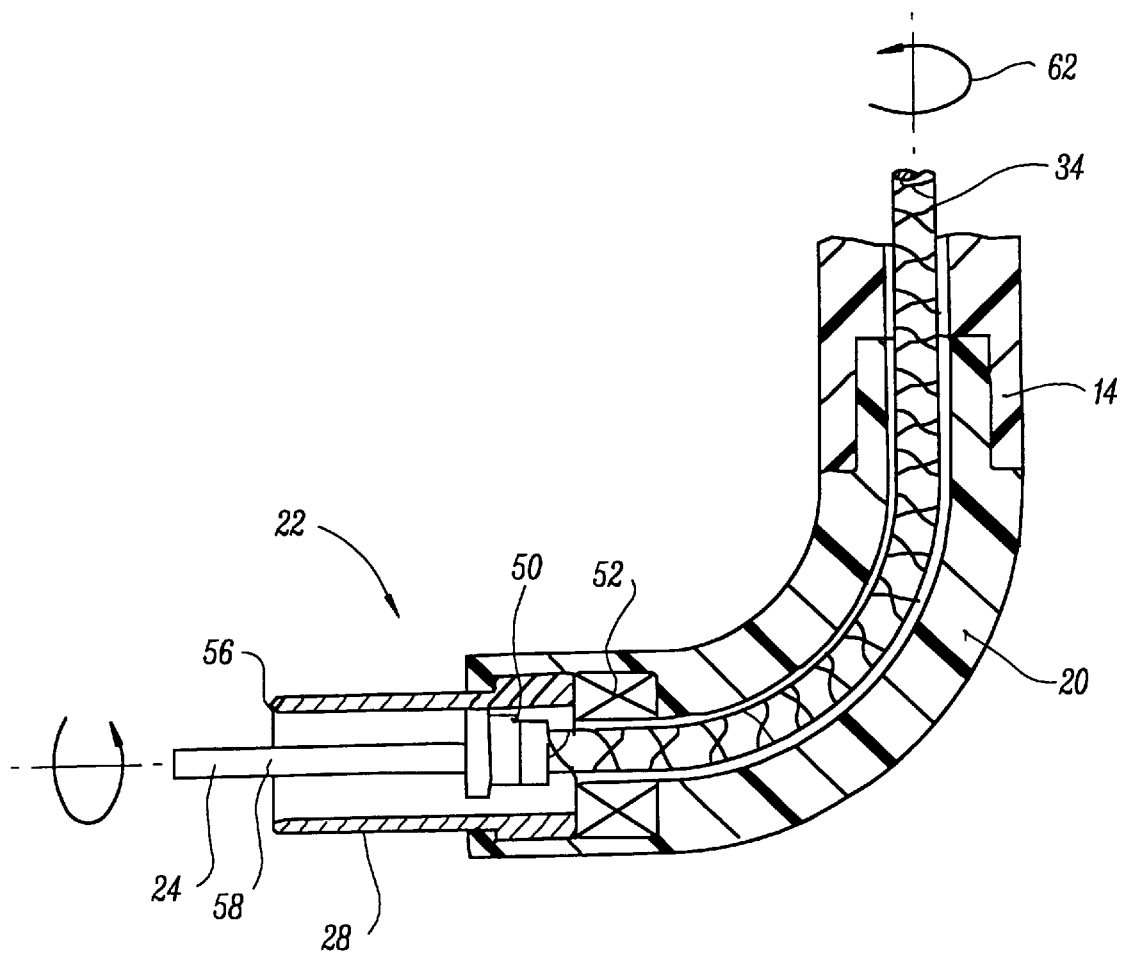
FIG. 5 is a view similar to FIG. 3, shown with the closed needle-grasping jaws in a rotated configuration.

Referring now to FIGS. 3–5, the clamping device 22 comprises the jaw elements 24 and 26, the collar 28, a connector 50 which joins the jaw elements 24 and 26 to the distal end of drive cable 34, and thrust bearing 52. The jaw elements 24 and 26 are connected together by a resilient hinge 54 which both permits the elements to pivot relative to one another and also maintains the jaws in a "normally open" configuration, as illustrated in FIG. 3. That is, the resilient hinge naturally holds the jaw elements 24 and 26 away from each other as shown in FIG. 3. Collar 28 defines a fixed surface 56 about the periphery of its proximal end. The fixed surface 56 engages a corresponding cam surfaces 58 formed on the radially outward sides of the jaw elements 24 and 26. In this way, when the drive cable 34 is retracted proximally, as is illustrated by arrows 60 in FIG. 4, interaction of the fixed surface 56 and the cam surfaces 58 will cause the jaws to close, also as illustrated in FIG. 4. As illustrated in FIG. 5, the jaws 24 and 26 may be rotated by rotating the drive cable 34 in the direction shown by arrow 62. The drive cable 34, of course, could also be rotated in the opposite direction, depending on the direction of rotation of the drive wheel 32. It will further be appreciated that the jaw elements 24 and 26 can be rotated in either their open configuration (FIG. 3) or their closed configuration (FIG. 4), or at any point therebetween. Moreover, jaw elements 24 and 26 can be opened or closed at any rotational position relative to needle support 20. The surfaces 56 and 58 permit free rotation and translation of the jaw members at all times.

As illustrated in FIGS. 3–5, the needle support 20 is formed as a separate component from the shaft 14, and joined thereto by conventional means, such as adhesives, fasteners, welding, or the like. The needle support will typically be formed to have a cross-sectional area and shape which are generally the same as those of the shaft 14, but this is not necessarily the case. The needle support 20 could assume a wide variety of configurations, so long as the drive cable 34 is deflected at the desired angle. As shown in FIGS. 3–5, the angle is about 90°. The angle could be greater or less than 90°, typically being between 45° and 135°, more typically being between 60° and 120°, and usually being between 70° and 110°, relative to the axis of the shaft 14.

Figure 8:
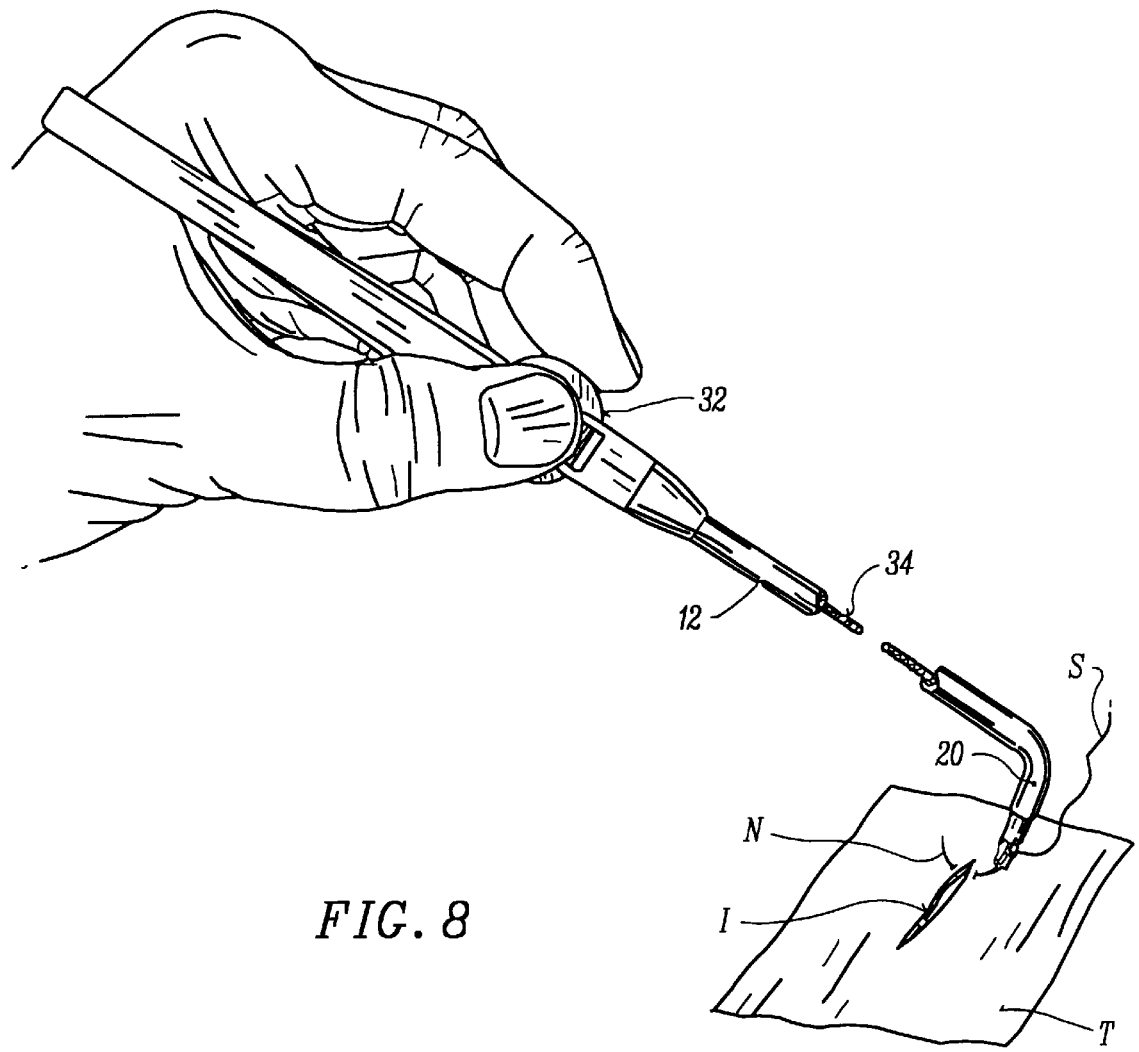

Referring now to FIGS. 6–8, use of the needle driver 10 for deploying a needle N in a suturing operation will be described. As shown in FIG. 6, the device 10 is normally inserted into a target location within a patient's body, typically within an open volume created by conventional thoracoscopic or laparoscopic techniques. In such cases, the shaft 12 of the device will be inserted through a trocar or other available access port which percutaneously penetrates into the surgical site. The device 10 is initially positioned so that jaws 24 and 26 are placed about the shank of needle N. The lever 30 is then depressed to grasp the needle shank, as shown in FIG. 7, such that the axis of curvature of the needle is generally parallel to the deflected axis of needle support 20. The shaft 12 is then manipulated so that the needle N lies approximate an incision I or other location in tissue T to be sutured. The needle N is then advanced through an arc having an axis parallel to the needle's axis of curvature by rotating rotatable wheel 32, resulting in the needle penetrating through the tissue and emerging from the tissue on the opposite side of the incision I, as shown in FIG. 8. The needle can then be released by raising lever 30, and the needle driver 10 used to regrasp needle N in jaws 24 and 26 near the tip of the needle. Needle N is then drawn through the tissue T, regrasped if necessary, and rotated again using rotatable wheel 32 to pass the needle N into tissue T. The process is repeated to pass additional throws of suture about the incision.

Figure 9:
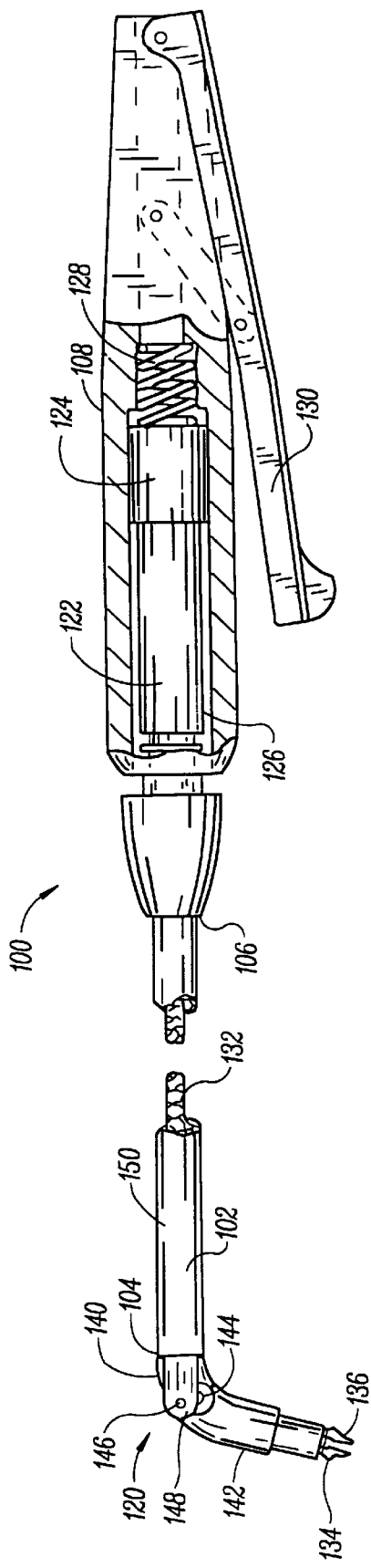
FIG. 9 illustrates an alternative embodiment of a surgical instrument constructed in accordance with the principles of the present invention, shown with a variably deflectable tip in a deflected configuration.
Figure 9A:
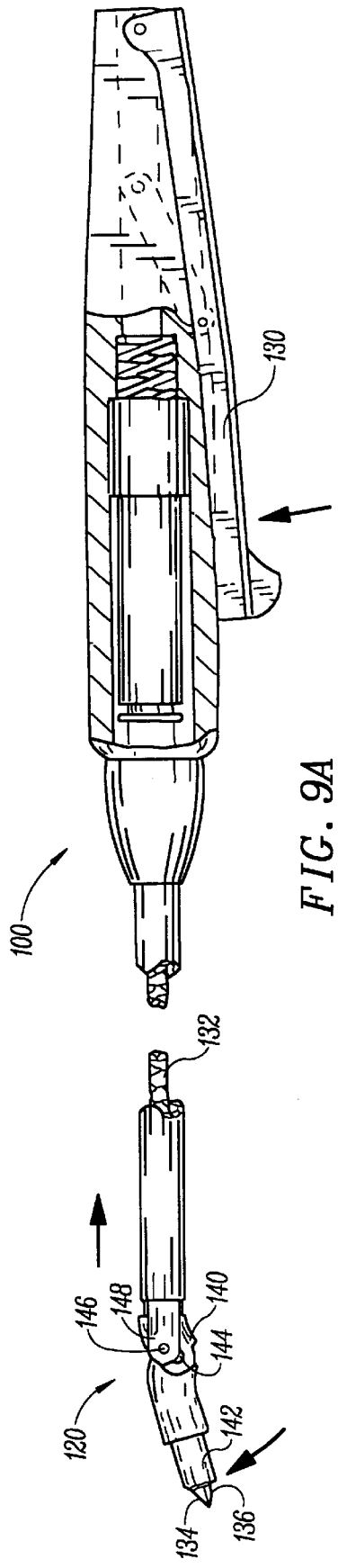
FIG. 9A illustrates the instrument of FIG. 9, shown with the variably deflectable tip in a relatively straight configuration.

Referring now to FIGS. 9 and 9A, an alternative device 100 constructed in accordance with the principles of the present invention will be illustrated. The device 100 includes a shaft 102 having a distal end 104 and a proximal end 106, a handle 108 secured to the proximal end 106 of the shaft, and an articulated support assembly 120 at a distal end of the shaft. A motor 122 and battery 124 are mounted in a receptacle 126 formed within the handle 108. The motor 122 and battery 124 are in tandem and urged in a distal direction by spring 128. Lever 130 is attached to the handle by a three-bar linkage, generally as described above. Closing of the lever 130 against the handle 108, as illustrated in FIG. 9A, causes the tandem assembly of the motor 122 and battery 124 to shift in the proximal direction. The motor 122 is attached to drive cable 132, causing jaws 134 and 136 to close, also as shown in FIG. 9A.

The articulated support assembly 120 comprises a stationary component 140 and a movable component 142 which are pivotably connected to each other by a pivot 144. A connecting pin 146 is attached to tongue 148 which in turn is connected to an outer coaxial sleeve 150 of the shaft 102. The stationary component 140 of the articulated assembly 120, in turn, is attached to an inner sleeve 152 of the shaft 102, as best seen in FIGS. 10 and 11. Cable 132 runs through the inner shaft 152. The outer sleeve 150 is reciprocatably mounted over the inner sleeve 152 and can be translated between a distally extended position, as shown in FIG. 9, to a proximally retracted condition, as shown in FIG. 9A. Translation of the outer shaft 150 between these two positions, in turn, causes the movable component 142 of the jaw to articulate from its deflected configuration, as shown in FIG. 9, to a more straightened configuration, as shown in FIG. 9A, which is suitable for positioning the distal portion of the device through a trocar sleeve or other relatively small access port or passage into the body cavity. Thus, the tip of the shaft 102 can be selectively deflected and straightened by axially translating the outer sleeve 150 distally and proximally, respectively. Articulated support assembly 120 is usually articulable through an angle of at least about 45°, preferably about 60° to 120°, relative to the longitudinal axis of the shaft 102. The flexible drive cable 132 passes through generally contiguous lumens formed in the stationary and movable components 140 and 142, as best seen in FIGS. 10 and 11. The drive cable remains rotatable in either position. It will be appreciated that a variety of other mechanical configurations could be arranged for providing a deflectable support member for the jaws 134 and 136.

The apparatus and method of the present invention may be used in a variety of procedures on a variety of anatomical structures. The apparatus and method are particularly useful for the closure of wounds, punctures, or incisions in structures such as the heart, aorta, bowel, and other vascular structures, as well as for performing vascular anastomoses in procedures such as coronary artery bypass grafting or bowel resection.

Although the foregoing invention has been described in some detail by way of illustration and example, for purposes of clarity of understanding, it will be obvious that certain changes and modifications may be practiced within the scope of the appended claims.

What is claimed is:

1. A needle driver comprising:
    a shaft having a proximal end, a distal end, and a lumen therebetween, wherein the shaft is fixed in a permanently deflected orientation and extends from a longitudinal axis at the proximal end to a deflected axis at the distal end, wherein the deflected axis extends transversely to the longitudinal axis, and the shaft is configured to remain in said deflected orientation during introduction of the needle driver into a patient's body and during use of the needle driver inside the body;
    a pair of jaws supported at the distal end of the shaft lumen, said jaws being pivotal relative to each other about an axis transverse to the deflected axis;
    a drive cable extending through the shaft lumen and connected to the pair of jaws;
    a handle disposed on the proximal end of the shaft;
    an actuator for moving the drive cable to pivot the jaws; and
    a rotator secured to the proximal end of the drive cable to selectively rotate the jaws about the deflected axis.

2. A needle driver as in claim 1, wherein the shaft comprises a generally straight proximal section having a length in the range from 5 cm to 20 cm, a maximum cross-sectional width in the range from 5 mm to 12 mm, and a deflected distal section.

3. A needle driver as in claim 2, wherein the distal end of the deflected distal section is radially offset from the axis of the proximal section of the shaft by a distance in the range from 5 mm to 15 mm.

4. A needle driver as in claim 1, wherein the deflected axis is oriented at an angle in the range from 45° to 135° relative to the longitudinal axis of the shaft.

5. A needle driver as in claim 1, wherein the actuator comprises a three bar linkage that includes a lever coupled to the handle, and a link coupled to a shuttle which is secured to the drive cable.

6. A needle driver as in claim 1, wherein the rotator comprises a wheel rotatably mounted on the shuttle and a gear attached to the proximal end of the drive cable, wherein the wheel engages the gear to rotate the drive cable.

7. A needle driver as in claim 1, wherein the rotator comprises a motor operatively coupled to the drive cable.

8. A needle driver comprising:
    a shaft having a proximal end, a distal end, and a lumen therebetween, wherein the shaft is fixed in a permanently deflected orientation and extends from a longitudinal axis at the proximal end to a deflected axis at the distal end, wherein the deflected axis extends transversely to the longitudinal axis, and the shaft is configured to remain in said deflected orientation during introduction of the needle driver into a patient's body and during use of the needle driver inside the body;
    a pair of jaws supported at the distal end of the shaft lumen, said jaws being pivotal relative to each other about an axis transverse to the deflected axis;
    a drive cable extending through the shaft lumen and connected to the pair of jaws;
    a handle disposed on the proximal end of the shaft; and
    an actuator for moving the drive cable to pivot the jaws;
    wherein the jaws are normally open, further comprising a fixed surface at the distal end of the shaft which engages cam surfaces on the jaws to close the jaws as the jaws are retracted into the shaft by the cable.

9. A needle driver as in claim 8, wherein the pivotally attached jaws are joined by a resilient hinge which holds the jaws open absent a closing force.

10. A needle driver comprising:
    a shaft having a proximal end, a distal end, and a lumen therebetween, wherein the shaft is fixed in a permanently deflected orientation and extends from a longitudinal axis at the proximal end to a deflected axis at the distal end, wherein the deflected axis extends transversely to the longitudinal axis, and the shaft is configured to remain in said deflected orientation during introduction of the needle driver into a patient's body and during use of the needle driver inside the body;
    a pair of jaws supported at the distal end of the shaft lumen, said jaws being pivotal relative to each other about an axis transverse to the deflected axis, the jaws being configured to hold a needle;
    a drive cable extending through the shaft lumen and connected to the pair of jaws;
    a handle disposed on the proximal end of the shaft; and
    an actuator for moving the drive cable to pivot the jaws,
    wherein the needle is curved about an axis of curvature and the jaws are configured to rotate the needle about the axis of curvature.

11. A needle driver comprising:
    a shaft having a proximal end, a distal end, a longitudinal axis and a lumen therebetween, wherein the shaft and lumen are fixedly deflected at their distal ends along a deflected axis which is transverse to the longitudinal axis, wherein the distal ends of the shaft and lumen remain deflected during use;
    a pair of jaws supported by the distal end of the shaft, said jaws being pivotal relative to each other about an axis transverse to the deflected axis;
    a drive cable extending through the shaft lumen and connected to the pair of jaws; and
    an actuator actuable from the proximal end of the shaft coupled to the drive cable to shift the jaws between an open configuration and a closed configuration and to rotate the jaws about the deflected axis.

12. A needle driver as in claim 11, wherein the shaft comprises a generally straight proximal section having a length in the range from 5 cm to 20 cm, a maximum cross-sectional width in the range from 5 mm to 12 mm, and a deflected distal section.

13. A needle driver as in claim 12, wherein the distal end of the deflected distal section is radially offset from the axis of the proximal section of the shaft by a distance in the range from 5 mm to 15 mm.

14. A needle driver as in claim 11, wherein the deflected axis is oriented at a fixed angle in the range from 45° to 135° relative to the longitudinal axis of the shaft.

15. A needle driver as in claim 11, wherein the jaws are normally open, further comprising a fixed surface at the distal end of the shaft which engages cam surfaces on the jaws to close the jaws as the jaws are retracted into the shaft by the cable.

16. A needle driver as in claim 15, wherein the pivotally attached jaws are joined by a resilient hinge which holds the jaws open absent a closing force.

17. A needle driver as in claim 11, wherein the actuator comprises a handle, a shuttle secured to the proximal end of the drive cable and slidably mounted within the handle, and a retractor secured between the handle and the shuttle to selectively retract the shuttle to close the jaws.

18. A needle driver as in claim 17, wherein the actuator further comprises a rotator secured to the proximal end of the drive cable to selectively rotate the jaws about the deflected axis.

19. A needle driver as in claim 17, wherein the retractor comprises a lever and a link connected as a three-bar linkage to retract the shuttle.

20. A needle driver as in claim 18, wherein the rotator comprises a wheel rotatably mounted on the shuttle and a gear attached to the proximal end of the drive cable, wherein the wheel engages the gear to rotate the drive cable.

21. A needle driver as in claim 18, wherein the rotator comprises a motor operatively coupled to the drive cable.

22. A needle driver as in claim 11, wherein the jaws are configured to hold a needle.

23. A needle driver as in claim 22, wherein the needle is curved about an axis of curvature and the jaws are configured to rotate the needle about said axis of curvature.

* * * * *